US009377412B2

(12) United States Patent
Shah et al.

(10) Patent No.: US 9,377,412 B2
(45) Date of Patent: Jun. 28, 2016

(54) ELECTRONIC DEVICE HAVING COMPONENTS WITH STRESS VISUALIZATION FEATURES

(71) Applicant: Apple Inc., Cupertino, CA (US)

(72) Inventors: Dhaval N. Shah, Fremont, CA (US); Joseph C. Poole, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 14/254,501

(22) Filed: Apr. 16, 2014

(65) Prior Publication Data

US 2015/0300961 A1 Oct. 22, 2015

(51) Int. Cl.
*G01N 21/88* (2006.01)
*G01M 5/00* (2006.01)
*G01N 21/45* (2006.01)
*G01N 33/00* (2006.01)

(52) U.S. Cl.
CPC ......... *G01N 21/8803* (2013.01); *G01M 5/0041* (2013.01); *G01N 21/45* (2013.01); *G01N 21/8851* (2013.01); *G01N 2033/0095* (2013.01)

(58) Field of Classification Search
CPC ............ G02B 2027/014; G06F 3/0414; B81B 2201/0264; B81B 3/00; H01L 41/1132; G01L 19/06; G01L 19/145; G01L 19/147; G01L 1/06; G01L 1/24; G01B 11/16; G01B 11/165; G01B 7/16; G01N 21/8803; G01N 21/45; G01N 21/8851; G01N 2033/0095; G01M 5/0041
See application file for complete search history.

(56) References Cited

U.S. PATENT DOCUMENTS

| | | | |
|---|---|---|---|
| 4,781,455 A * | 11/1988 | Machler | G01L 1/24 356/32 |
| 6,781,702 B2 | 8/2004 | Giannakopoulos et al. | |
| 6,924,497 B2 | 8/2005 | Suresh et al. | |
| 7,311,008 B2 | 12/2007 | Langer et al. | |
| 7,930,113 B1 | 4/2011 | Huang et al. | |
| 7,966,135 B2 | 6/2011 | Rosakis et al. | |
| 2008/0309623 A1 * | 12/2008 | Hotelling | C12N 15/86 345/173 |
| 2010/0225483 A1 * | 9/2010 | Scheucher | G06K 7/0095 340/572.3 |
| 2013/0057805 A1 * | 3/2013 | Minoura | G02B 6/0088 349/62 |
| 2013/0320467 A1 * | 12/2013 | Buchanan | G01N 29/022 257/419 |
| 2013/0342846 A1 * | 12/2013 | Campagne et al. | 356/450 |
| 2014/0049464 A1 * | 2/2014 | Kwak | G06F 3/0487 345/156 |

FOREIGN PATENT DOCUMENTS

SE             EP 2685358 A1 * 1/2014 ............ G06F 3/0414

* cited by examiner

*Primary Examiner* — Julio J Maldonado
*Assistant Examiner* — Farun Lu
(74) *Attorney, Agent, or Firm* — Treyz Law Group, P.C.; G. Victor Treyz; Zachary D. Hadd

(57) ABSTRACT

An electronic device may have housing structures, electrical components, and other electronic device structures. Stress sensing structures may be formed using coatings on these electronic device structures. Stress sensing structures may have strip-shaped links that extend between pads or may be formed from blanket films. A stress sensing coating may be formed from a transparent thin film. The transparent thin film may be illuminated with monochromatic light while a video camera captures video images of resulting optical interference patterns. The video images may be captured during a test in which a device structure is exposed to stress from an impact between the device and an external object. Stress sensing coatings may also be formed from layers of material that develop cracks upon exposure to stress. Stress sensing structures may be used to evaluate stress during tests and to monitor stress during normal device use.

18 Claims, 12 Drawing Sheets

ELECTRONIC DEVICE HAVING COMPONENTS WITH STRESS VISUALIZATION FEATURES

BACKGROUND

This relates generally to electronic devices, and, more particularly, to structures for assessing stress levels in electronic device components.

Electronic devices include components such as housing structures, electrical components, displays, and other device structures. Some structures may be sensitive to stress. Stress may be generated during use of an electronic device. For example, drop events and other impact events may generate considerable amounts of stress.

It can be challenging to assess stress levels in electronic device structures. With one approach, a test device may be covered with an array of dots. A high speed camera can be used to record the test device as the test device is dropped onto a hard surface. By analysing the positions of the dots during the test event, the amount by which the device flexes and experiences stress during impacts can be determined. This type of approach may be used to gather information that helps device designers to design more robust devices, but is relatively insensitive and cannot be used to assess how much stress is encountered by a device during normal use.

It would be desirable to be able to provide improved techniques for assessing stress levels in the structures of an electronic device.

SUMMARY

An electronic device may have housing structures, electrical components, and other electronic device structures. Stress sensing structures may be formed on these electronic device structures. The stress sensing structures may be used to measure stress levels during impact tests or may be used to monitor stress levels encountered during use of an electronic device by a user.

The stress sensing structures may be formed from thin-film coatings. Stress sensing structures may have strip-shaped links that extend between pads or may be formed from blanket films. Films may be formed on components such as integrated circuits, displays, housing structures, and other structures in an electronic device.

A stress sensing coating may be formed from a transparent thin film. The transparent thin film may be illuminated with monochromatic light while a video camera captures video images of resulting optical interference patterns. The video images may be captured during a test in which a device structure is exposed to stress from an impact between the device and an external object.

Stress sensing coatings may also be formed from layers of material that develop cracks upon exposure to stress. For example, an inorganic layer of material or other layer that cracks when exposed to stresses greater than a predetermined stress level may be used as a stress sensing coating.

DETAILED DESCRIPTION

Stress sensing structures may be used in ascertaining whether a structure in an electronic device such as a housing or a device component has been subjected to excessive stress.

The stress sensing structures may also be used in gathering detailed data on the stresses experienced by a device. The stress sensing structures may be used during stress testing and/or normal operation of a device. Stress sensing structures may be formed using blanket coatings and using patterned layers of material.

Figure 1:
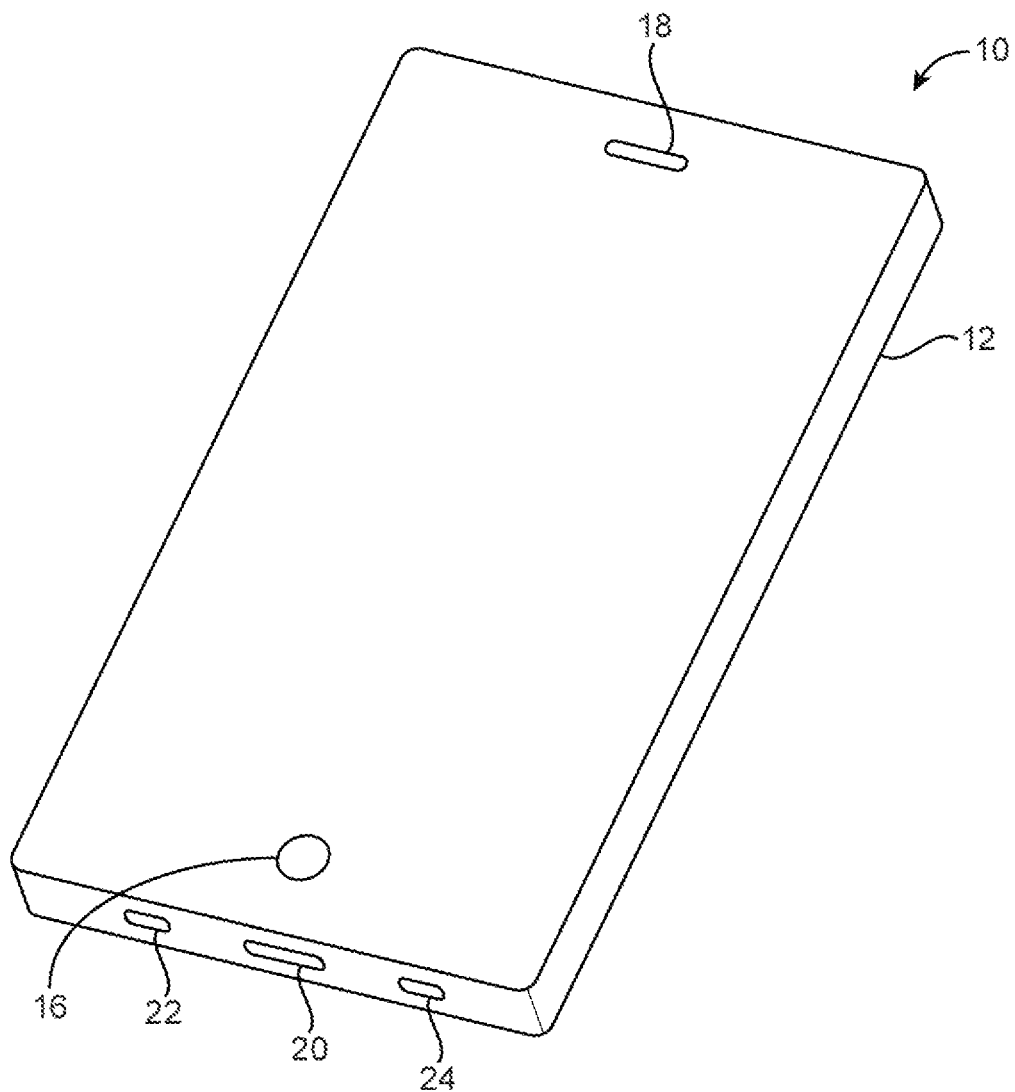
FIG. 1 is a perspective view of an illustrative electronic device in accordance with an embodiment.

FIG. 1 is a perspective view of an illustrative electronic device of the type that may be include stress sensing structures. An electronic device such as electronic device 10 of FIG. 1 may be a computing device such as a laptop computer, a computer monitor containing an embedded computer, a tablet computer, a cellular telephone, a media player, or other handheld or portable electronic device, a smaller device such as a wrist-watch device, a pendant device, a headphone or earpiece device, or other wearable or miniature device, a television, a computer display that does not contain an embedded computer, a gaming device, a navigation device, an embedded system such as a system in which electronic equipment with a display is mounted in a kiosk or automobile, equipment that implements the functionality of two or more of these devices, or other electronic equipment. The configuration of device 10 that is shown in FIG. 1 (e.g., a portable device configuration in which device 10 is a cellular telephone, media player, tablet computer, or other portable computing device) is shown as an example. Other configurations may be used for device 10 if desired.

Device 10 may have one or more displays such as display 14 mounted in housing structures such as housing 12. Housing 12 of device 10, which is sometimes referred to as a case, may be formed of materials such as plastic, glass, ceramics, carbon-fiber composites and other fiber-based composites, metal (e.g., machined aluminum, stainless steel, or other metals), other materials, or a combination of these materials. Device 10 may be formed using a unibody construction in which most or all of housing 12 is formed from a single structural element (e.g., a piece of machined metal or a piece of molded plastic) or may be formed from multiple housing structures (e.g., outer housing structures that have been mounted to internal frame elements or other internal housing structures).

Display 14 may be a touch sensitive display that includes a touch sensor or may be insensitive to touch. Touch sensors for display 14 may be formed from an array of capacitive touch sensor electrodes, a resistive touch array, touch sensor structures based on acoustic touch, optical touch, or force-based touch technologies, or other suitable touch sensor components.

Display 14 for device 10 includes display pixels formed from liquid crystal display (LCD) components or other suitable display pixel structures such as organic light-emitting diode display pixels, electrophoretic display pixels, plasma display pixels, etc.

Electronic device 10 may include control circuitry. The control circuitry of device 10 may include storage and processing circuitry for controlling the operation of device 10. Control circuitry in device 10 may, for example, include storage such as hard disk drive storage, nonvolatile memory (e.g., flash memory or other electrically-programmable-read-only memory configured to form a solid state drive), volatile memory (e.g., static or dynamic random-access-memory), etc. Control circuitry in device 10 may include processing circuitry based on one or more microprocessors, microcontrollers, digital signal processors, baseband processors, power management units, audio codec chips, application specific integrated circuits, etc.

Input-output devices in device 10 may be used to allow data to be supplied to device 10 and to allow data to be provided from device 10 to external devices. Input-output devices for device 10 may also include input-output components with which a user can control the operation of device 10. A user may, for example, supply commands through input-output devices in device 10 and may receive status information and other output from device 10 using the output resources of input-output devices in device 10.

Input-output devices for device 10 may include sensors and status indicators such as an ambient light sensor, a proximity sensor, a temperature sensor, a pressure sensor, a magnetic sensor, an accelerometer, a touch sensor, a fingerprint sensor, and light-emitting diodes and other components for gathering information about the environment in which device 10 is operating and providing information to a user of device 10 about the status of device 10. Device 10 may include audio components such as speakers and tone generators for presenting sound to a user of device 10 and microphones for gathering user audio input. The input-output devices of device 10 may include one or more displays. Displays may be used to present images for a user such as text, video, and still images. Sensors in device 10 may include a touch sensor array that is formed as one of the layers in display 14. During operation, user input may be gathered using buttons and other input-output components such as touch pad sensors, buttons, joysticks, click wheels, scrolling wheels, touch sensors such as a touch sensor array in a touch screen display or a touch pad, key pads, keyboards, vibrators, cameras, and other input-output components. The input-output devices of device 10 may include wired and wireless communications circuitry (e.g., circuitry to support digital data communications, a radio-frequency transceiver and antennas for supporting wireless communications, etc.).

Display 14 may have an outermost layer such as a layer of glass or plastic. The outermost layer may be a display cover layer. Openings may be formed in the outermost layer of display 14 such as an opening for menu button 16 and/or speaker port 18. Housing 12 may also be provided with openings such as microphone port 22, connector port 20, and speaker port 24 (as examples).

Device 10 may be subjected to stress during normal use. For example, a user of device 10 may inadvertently drop device 10 onto a hard surface. When device 10 experiences an impact event, components in device 10 and portions of housing 12 (e.g., portions of housing 12 near stress concentrating features such as openings 16, 18, 22, 20, and 24 or other stress concentrating features) may experience undesired levels of stress. It may be helpful to monitor for stresses such as these to facilitate repair or to determine when device 10 has been subjected to such a high level of stress that repair is not feasible. If desired, device 10 may be intentionally subjected to stress during testing. Test results may be used to design enhancements that help devices better withstand stress in the future.

Stress sensing structures may be provided in device 10 that can be used for monitoring stress in normal use and/or during testing. The stress sensing structures may include structures based on blanket thin films or stress sensors formed form patterned stress sensing strips of material (e.g., a patterned coating or other layer of material).

Figure 2:
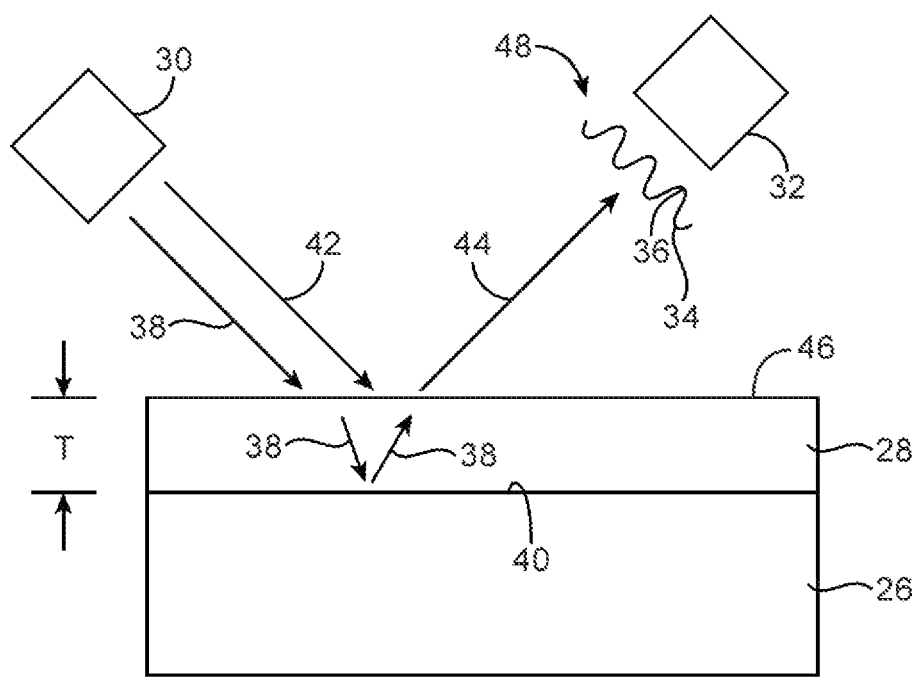
FIG. 2 is a side view of a device structure with a thin-film coating and associated optical equipment for measuring stress in the structure using light reflected from the coating in accordance with an embodiment.

An illustrative stress sensing arrangement of the type that may be used in device 10 is shown in FIG. 2. As shown in FIG. 2, a coating such as coating 28 may be formed on a structure such as structure 26. Structure 26 may be formed from metal, plastic, carbon-fiber composite material or other fiber composites, ceramic, glass, other materials, or combinations of these materials. Structure 26 may be formed from interior and/or exterior structures in device 10. For example, structure 26 may include some or all of display 14 (e.g., a display cover layer, a display layer that forms some or all of the active light-emitting structure in display 14, etc.), some or all of housing 12, a connector, an integrated circuit, an electrical device such as a sensor or switch or other circuit component, a mechanical device such as a support structure, bracket, frame member, or other structural feature in device 10, an audio component, a cable or other signal path structure, a package for a component, a substrate for a component, a printed circuit, or other structure in device 10.

Coating 28 may be an optical thin-film coating formed from one or more layers. In the example of FIG. 2, coating 28 has been formed from a single layer of material on the upper surface of structure 26. Coating 28 may be formed from a dielectric such as glass, plastic, ceramic, or other material. If desired, coating 28 may be formed from a transparent material (e.g., clear glass, clear plastic, etc.). With this type of arrangement, light may be reflected from surface 40 of structure 26 after having passed through coating 28. Other light may be reflected from surface 46 of coating 28. Light interference may result in detectable fringe patterns that can be used to help measure stress.

As shown in FIG. 2, stress may be monitored using stress monitoring equipment such as light source 30 and light detector 32. Light source 30 may be a monochromatic light source such as a monochromatic light-emitting diode or a lamp with a filter that passes monochromatic light. Configurations for light source 30 that use light of more than one wavelength (color) may also be used. Light from light source 30 may be visible light, infrared light, and/or ultraviolet light.

Light detector 32 may be a video camera (e.g., a video camera capable of capturing video images with a frame rate sufficient to monitor relatively rapid events such as impact events during testing), may be a photodetector or other light sensor that forms part of a reflectometer, may be a camera, or may be other equipment that measures light.

Coating 28 may have a thickness T that is relatively small (e.g., on the order of a fraction of a wavelength of light to multiple wavelengths of light). Coatings such as these are sometimes referred to as thin film coatings. The relatively small thickness of coating 28 allows coating 28 to produce thin film interference patterns such as pattern 48 when illuminated with light from light source 30. As shown in FIG. 2, light from light source 30 includes light rays such as light ray 38 and light ray 42. Some light from light source 30 such as light ray 38 passes into coating 28 through surface 46 of coating 28 and reflects from the interface between structure 26 and coating 28. Other light from light source 30 such as light ray 42 reflects directly off of surface 46 of coating 28. Reflected light 44 from coating 28 and structure 26 therefore includes both types of reflected light—light reflected directly from surface 46 and light reflected from surface 40. Constructive and destructive interference between these two types of reflected light gives rise to light and dark bands such a light fringe 36 and dark fringe 34 in reflected light pattern 48. The number of bands and the spatial frequency of the bands in the interference pattern (i.e., the number of light and dark bands in pattern 48 of FIG. 2 and the spacing between the light and dark bands) reflect the current thickness T of coating 28. The value of T is affected by stress, so measurements of light pattern 48 reveal real time information on the level of stress in coating 28 and structure 26.

Figure 3:
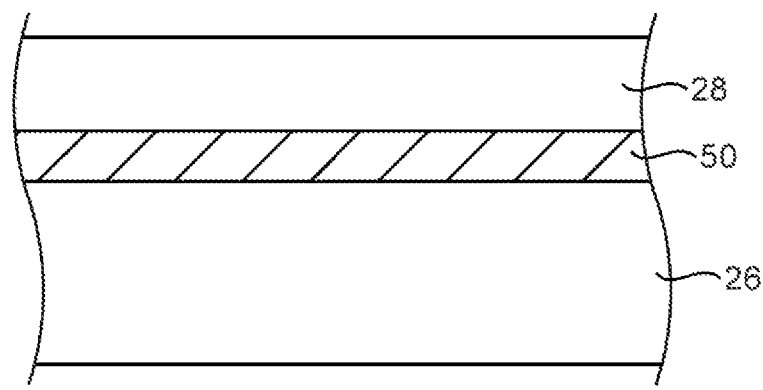
FIG. 3 is a cross-sectional side view of an illustrative device structure that has been coated with a thin-film coating and that includes an opaque surface preparation layer under the thin-film coating in accordance with an embodiment.

If desired, one or more additional clear layers of material (i.e., sublayers) may be included in coating 28 and/or a surface preparation coating layer may be formed between a clear coating such as coating 28 and underlying structures such as structure 26. As shown in FIG. 3, for example, a surface preparation layer such as layer 50 may be interposed between structure 26 and coating 28. Layer 50 may be formed from plastic (e.g., a black ink or other dark polymer), glass, ceramic, metal, etc. In situations in which coating 28 has an index of refraction similar to that of structure 26, the inclusion of surface preparation layer 50 on structure 26 may ensure that there is a sufficient index of refraction difference between coating 28 and underlying structures to support the formation of sufficiently detectable light and dark bands in interference pattern 48.

Figure 4:
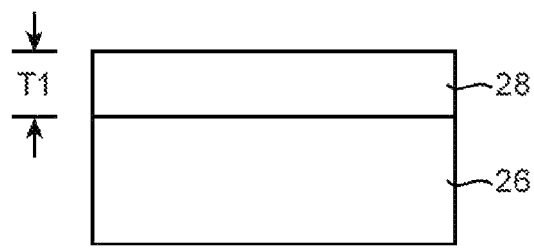
FIG. 4 is a cross-sectional side view of an illustrative structure to be monitored for stress that has been coated with a thin-film coating in accordance with an embodiment.
Figure 5:
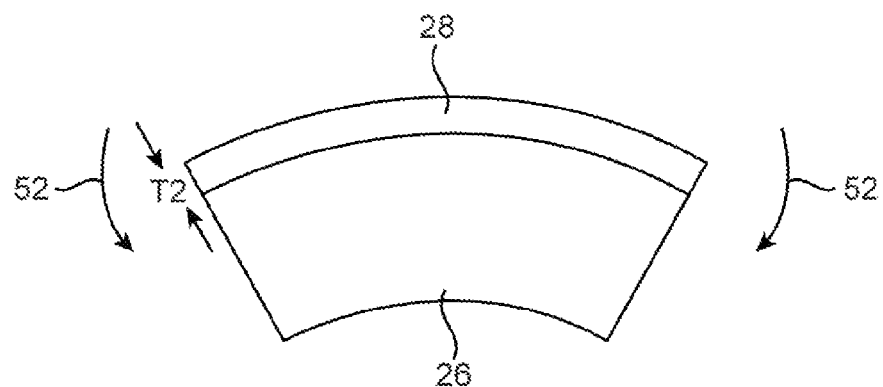
FIG. 5 is a cross-sectional side view of the illustrative structure of FIG. 4 that has been bent downwards creating tensile stress in the thin-film coating in accordance with an embodiment.
Figure 6:
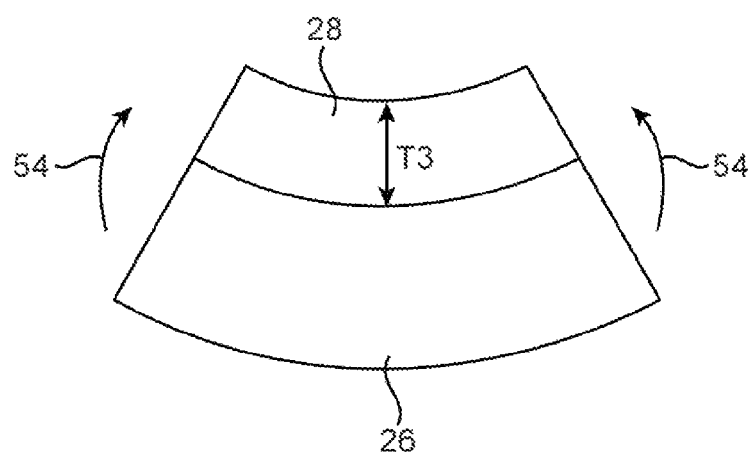
FIG. 6 is a cross-sectional side view of the illustrative structure of FIG. 4 that has been bent upwards creating compressive stress in the thin-film coating in accordance with an embodiment.
Figure 7:
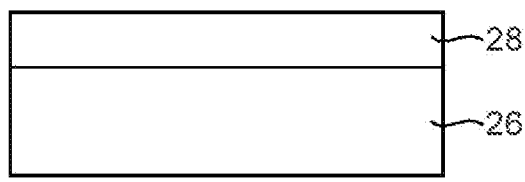
FIG. 7 is a cross-sectional side view of an illustrative structure that has been coated with a thin-film coating that cracks when subjected to a given amount of stress in accordance with an embodiment.

The impact of stress on thickness T of coating 28 is illustrated in FIGS. 4, 5, and 6. In the situation illustrated in FIG. 4, no outside forces have been applied to structure 26, so structure 26 is not bent and the thickness T of stress-sensing optical coating 28 has its nominal thickness value of T1. In some situations, structure 26 is subjected to forces that thin coating 28. As shown in FIG. 5, for example, the ends of structure 26 may be bent downwards in direction 52 so that coating 28 is placed under tensile stress. This thins coating 28 so that the thickness T of coating 28 has a thinned value of T2 that is less than T1. In the illustrative configuration of FIG. 6, structure 26 has been subjected to forces that cause the ends of structure 26 to bend upwards in direction 54, thereby placing coating 28 under compressive stress. This thickens coating 28 so that the thickness T of coating 28 has a thickened value of T3 that is greater than T1.

The optical interference pattern 48 that is detected by light sensor 32 (e.g., the number and positions of the light and dark light interference bands in pattern 48) depends on the value of thickness T. By monitoring and analyzing pattern 48, the monitoring equipment of FIG. 2 may monitor the value of T as a function of time and may therefore monitor the stress levels in coating 28 and structure 26 as a function of time. In this type of stress monitoring configuration, coating 28 may or may not exhibit a permanent change due to the application of stress.

If desired, coating 28 may be configured to exhibit permanent detectable changes in response to applied forces. For example, coating 28 may be formed from a material that exhibits cracking when exposed to an amount of stress that exceeds a predetermined stress threshold. Coating 28 may be visually examined to determine whether some or all of coating 28 has been exposed to stress in excess of the threshold.

This type of arrangement is illustrated in FIGS. 7, 8, 9, and 10. Initially, structure 26 and coating 28 are not subjected to external force and have the appearance shown in FIG. 7. Thickness T of coating 28 may have a nominal value of T1. Coating 28 of FIG. 7 may or may not be formed form a clear material.

Figure 8:
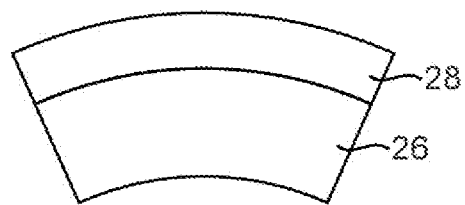
FIG. 8 is a cross-sectional side view of the illustrative structure of FIG. 7 being bent to create an amount of stress in the thin-film coating that is less than the given amount of stress in accordance with an embodiment.
Figure 9:
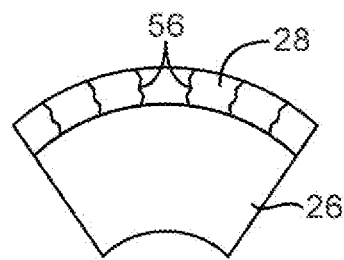
FIG. 9 is a cross-sectional side view of the illustrative structure of FIG. 7 being bent sufficiently to create stress in the thin-film coating that exceeds the given amount of stress in accordance with an embodiment.
Figure 10:
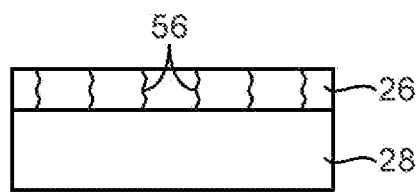
FIG. 10 is a cross-sectional side view of the illustrative structure of FIG. 9 showing how stress cracks in the thin-film coating may remain visible after the structure is no longer being bent in accordance with an embodiment.

During testing or during use of device 10 in the field, structure 26 and coating 28 may be exposed to forces that generate tensile and/or compressive stress in coating 28. For example, structure 26 and coating 28 may bend as shown in FIG. 8. If the amount of bending of structure 26 and 28 is sufficient, the tensile or compressive stress in coating 28 will be sufficient to damage coating 28. For example, coating 28 may develop cracks 56, as shown in FIG. 9. Coating 28 may be formed from a material that does not naturally heal when returned to an unstressed condition. For example, coating 28 may be formed form a layer of silicon oxide, silicon nitride, or other inorganic material or may be formed from an organic film such as a hard polymer film that is permanently cracked when stress exceeds a predetermined value. As a result, even when the forces on device 10 have been removed (e.g., after a drop event or other impact event has occurred and device 10 is no longer being stressed), detectable cracks 56 may remain in coating 28, as shown in FIG. 10. The location and density of cracks 56 may be ascertained by unaided visual inspection and/or inspection using a microscope or other visual aid (e.g., image processing equipment, electron microscope equipment, optical microscope equipment, a magnifier, etc.).

Figure 11:
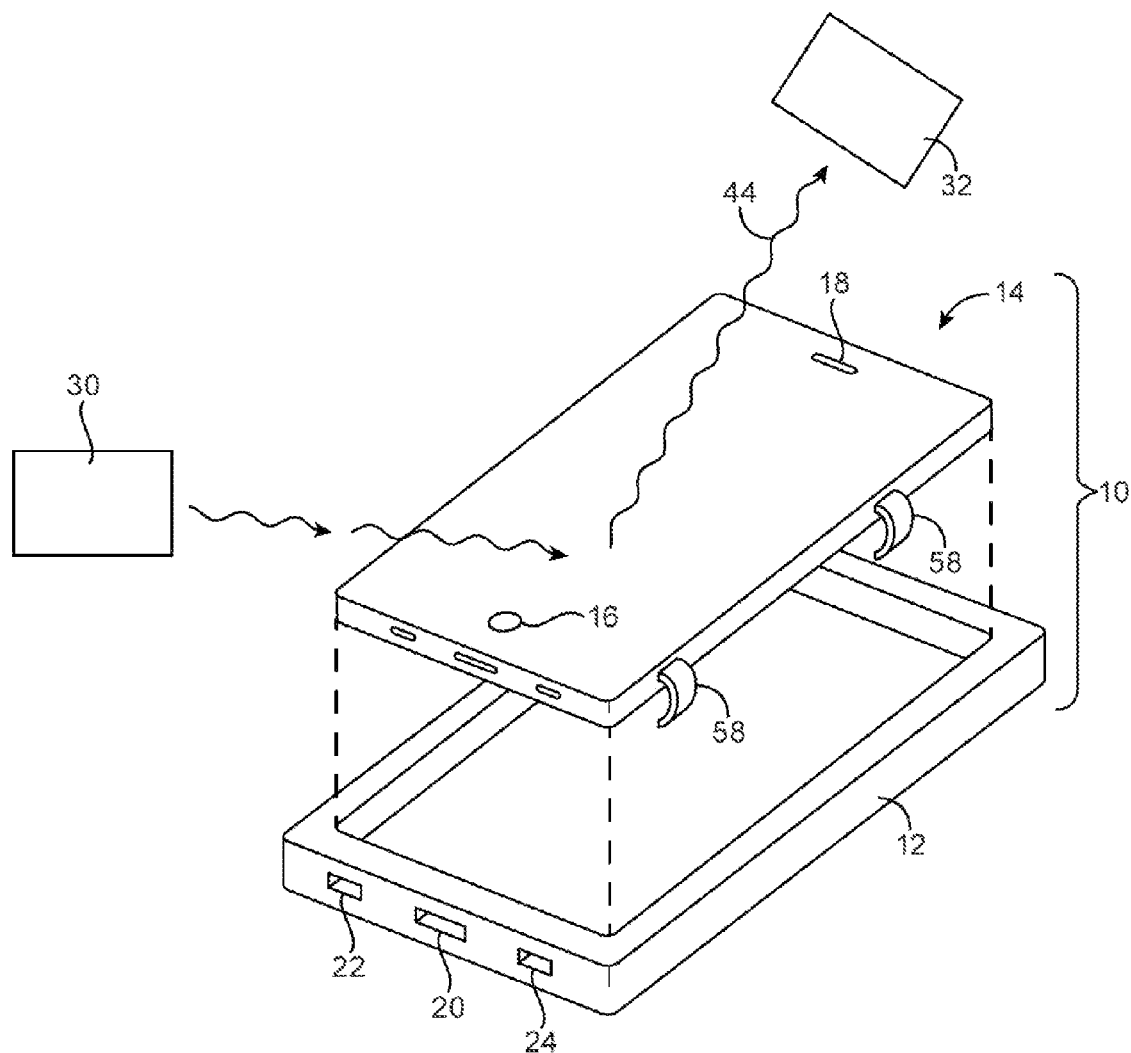
FIG. 11 is a perspective view of an illustrative electronic device being monitored with optical stress monitoring equipment that is reflecting light from a transparent thin-film coating on a display in the electronic device in accordance with an embodiment.
Figure 12:
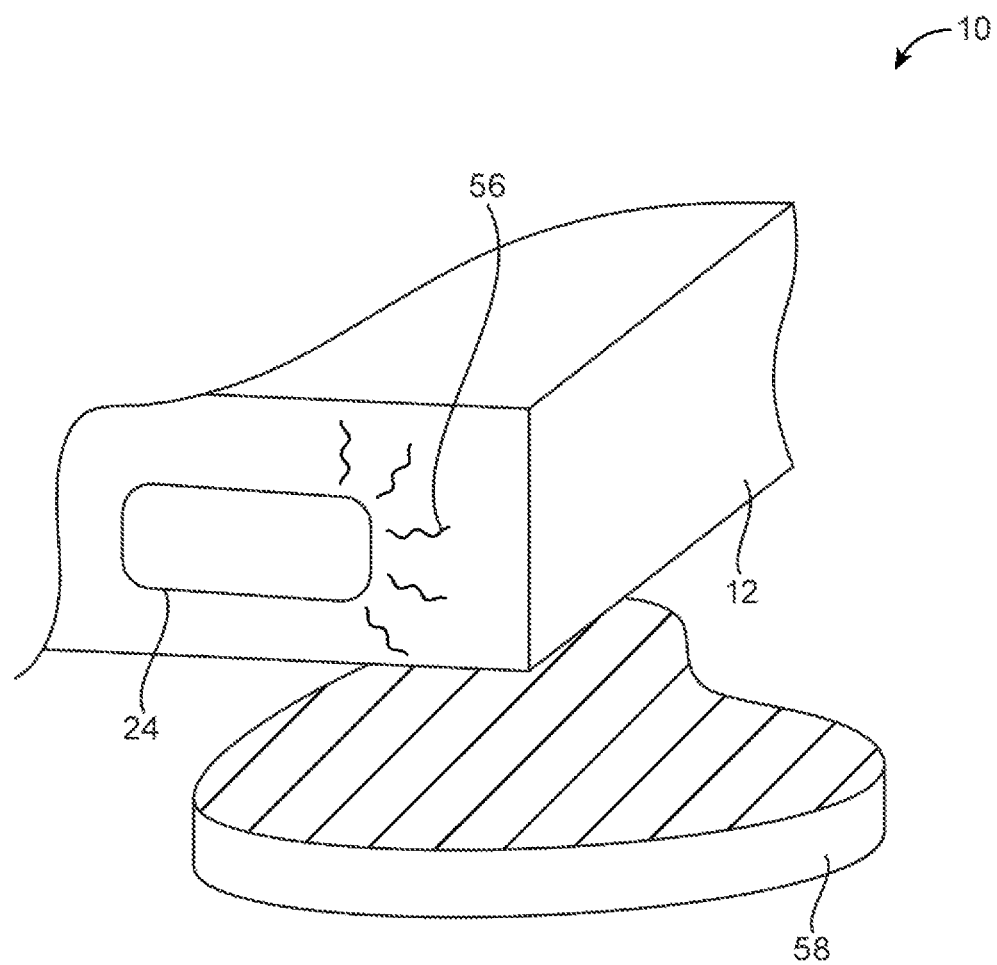
FIG. 12 is a perspective view of a corner portion of the electronic device of FIG. 1 during contact between the electronic device and an external object that is creating stress within the housing of the electronic device in accordance with an embodiment.

FIG. 11 is an exploded perspective view of device 10 in an illustrative configuration in which coating 28 has been formed on the surface of display 14. In this type of scenario, structure 26 corresponds to one or more layer of display 14 (e.g., one or more glass and/or plastic layers such as a display cover glass, a color filter layer, a thin-film transistor layer, a polarizer layer, or other display layers in display 14). Coating 28 may be a layer of inorganic material or other material on the surface of display 14. Display 14 is shown in an unassembled state in FIG. 11. During assembly, clips 58 or other mounting structures may be used to mount display 14 within housing 12 of electronic device 10. By shining light from light source 30 onto display 14 while light detector 32 monitors reflected light 44, stresses that are induced in display 14 may be monitored. For example, stresses in display 14 may be monitored during assembly of display 14 into housing 12. Stresses may also be monitored following assembly (e.g., by monitoring reflected light 44 from display 14 during an intentional drop event). If desired, display 14 may be provided with a coating that exhibits cracks upon being exposed to excessive stress, such as the coating described in connection with FIGS. 7, 8, 9, and 10. A surface preparation layer may, if desired, be formed under coating 28.

Device housing 12 and display 14 may have openings. The openings may tend to concentrate stress and may therefore sometimes be referred to as stress concentrating openings. Other features in device 10 (e.g., locally thickened or thinned portions of housing 12, display 14, or other structures in device 10) may also serve as stress concentrators. Because stress is concentrated in the vicinity of these features, it may be helpful to monitor the state of coating 28 in the vicinity of these features. In a transparent optical thin-film coating arrangement, light detector 32 is used to monitor for light interference patterns in the vicinity of the openings or other stress concentrators. In a crack sensitive coating arrangement, coating 28 may be inspected in the vicinity of the stress concentrator. Such visual inspection may reveal cracks such as cracks 56 adjacent to an opening in housing 12 such as illustrative opening 24 that were created when housing 12 struck external object 58.

Figure 13:
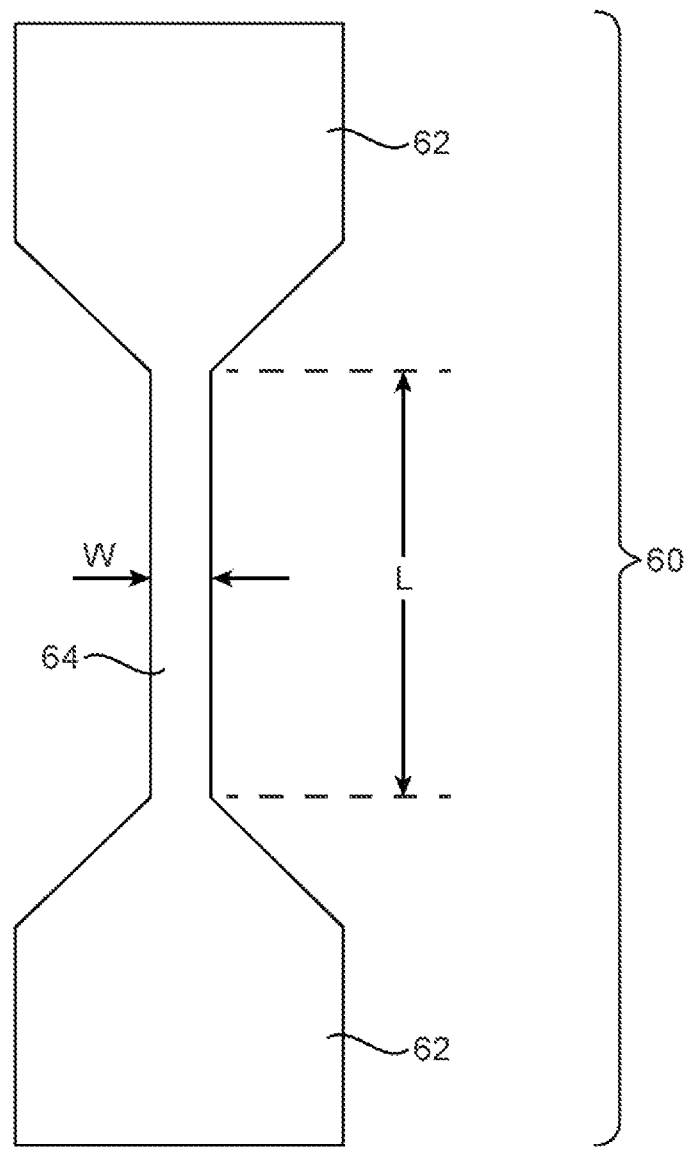
FIG. 13 is a diagram of an illustrative stress sensor of the type that may be used to monitor stress in an electronic device in accordance with an embodiment.

If desired, stress sensing structures may be formed from a patterned portion of a stress sensitive coating. This type of sensor arrangement is shown in FIG. 13. In the example of FIG. 13, stress sensor structure 60 has anchoring structures such as anchor pads 62. A more fragile and therefore more sensitive portion of the stress sensor structure may be formed between respective anchoring pads 62. As an example, an elongated strip of material such as elongated strip 64 or other link structure may be formed that extends between pads 62. The shape of the strip of material that extends between pads 62 may have any suitable shape (e.g., a straight unbent shape such as the elongated rectangular strip shape of FIG. 13, a meandering path shape such as a shape with straight sections and/or curved sections and one or more bends, or other suitable shape). In the FIG. 13 configuration, stress-sensing link 64 has an elongated strip shape with a width W that is less than length L. Width W is also significantly less than the lateral dimensions of pads 62. As a result, when more than a predetermined amount of stress is applied to sensor structure 60 of FIG. 13, link 64 serves as the weakest link in sensor 60 and may fail (e.g., crack), whereas anchor pads 62 will generally remain uncracked—. Sensor structure 60 may be electrically monitored (e.g., by forming structure 62 from a conductive material having a resistance that can be monitored using monitoring circuitry in device 10 or external to device 10) or may be monitored using unaided visual inspection or visual inspection equipment (e.g., visual inspection equipment such as equipment that includes a microscope, a video camera or still camera, etc.).

Figure 14:
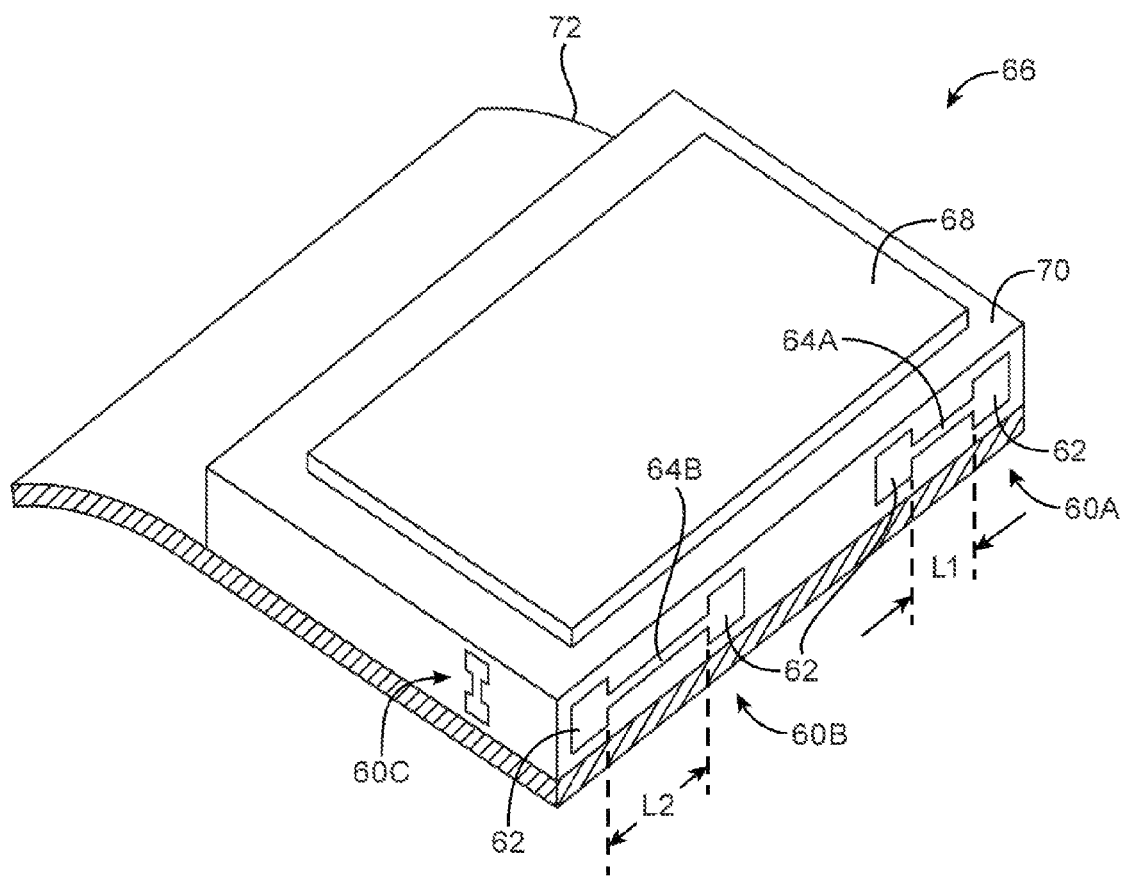
FIG. 14 is a perspective view of an illustrative electronic device with stress sensors along a side of the electronic device in accordance with an embodiment.

Structures such as sensor structure 60 may be incorporated into device 10 on exterior portions of housing 12, on interior portions of housing 12, on portions of display 14, on support structures and other internal components, etc. In the example of FIG. 14, structures 60 have been incorporated onto an internal device component such as component 66. Component 66 may include device 68 on substrate 70. Device 68 may be an integrated circuit or other electrical component. Substrate 70 may be a ceramic substrate, a plastic carrier, or other support structure for device 68. Substrate 70 may include metal traces for routing signals between device 68 and printed circuit 72. Printed circuit 72 may be a rigid printed circuit board (e.g., a printed circuit board formed from fiberglass-filled epoxy or other rigid printed circuit board material) or may be a flexible printed circuit (e.g., a printed circuit formed from a flexible layer of polyimide or a sheet of other flexible polymer material).

Sensor structures 60 may have different shapes and sizes corresponding to different respective stress sensing thresholds. For example, sensors such as sensor 60A and sensor 60B may have stress-sensing links such as strips 64A and 64B that have different respective dimensions (e.g., different lengths L1 and L2, different widths, etc.). The different shapes and sizes of the structures forming links 64A and 64B may cause sensors 60A and 60B to have different stress sensing thresholds. In particular, stress sensor 60A may remain intact up to a stress sensing threshold value that is different than the stress sensing threshold of stress sensor 60B. By examining which of multiple stress sensors in component 66 have severed links (or links with cracks or links that otherwise exhibit changes that indicate that their stress threshold has been exceeded) the level of stress that has been imposed on device 68 may be evaluated.

Stress sensors may be incorporated into one or more portions of component 66 (e.g., on device 68, on substrate 70, on printed circuit 72, etc.). Moreover, the orientations of different stress sensors may be different. As an example, stress sensor 60C may be oriented to respond to vertical stresses on structure 70, whereas stress sensors 60A and 60B may be oriented so that they respond to horizontal stress. Stress sensors such as sensors 60A, 60B, and 60C may be formed by depositing a coating and patterning the coating using photolithography or other techniques, by printing or otherwise forming sensors 60A, 60B, and 60C in a desired shape, or by attaching prepatterned structures using a layer of adhesive (as examples).

Figure 15:
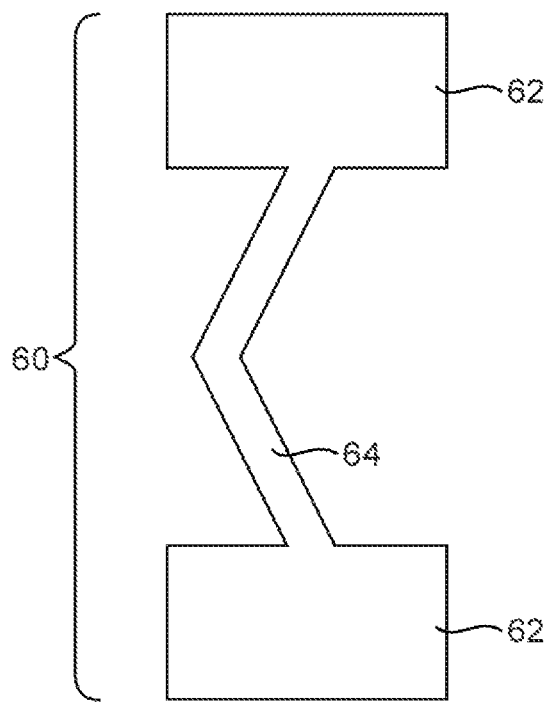
FIG. 15 is a diagram of an illustrative stress sensor having a stress sensing link formed from a strip-shaped portion of a layer of material that extends between a pair of respective anchor pads and that has a bend in accordance with an embodiment.
Figure 16:
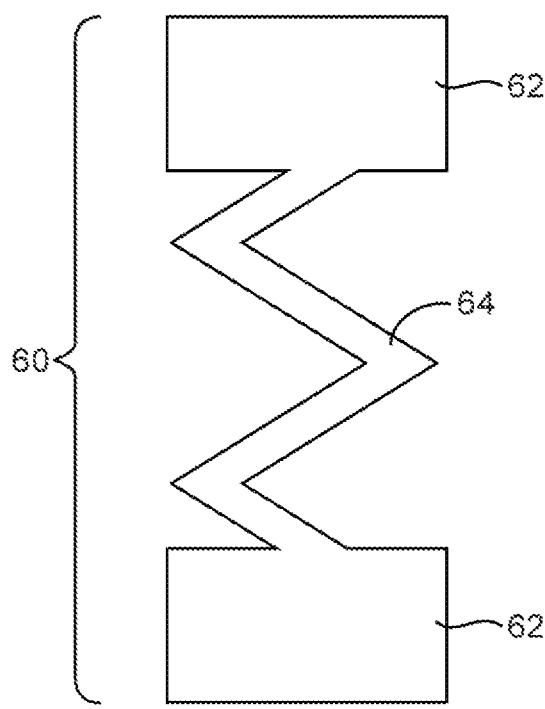
FIG. 16 is a diagram of an illustrative stress sensor having a stress sensing strip that extends between a pair of respective anchor pads and that has multiple bends in accordance with an embodiment.

If desired, stress sensing structures such as structures 60A, 60B, and 60C may be provided with links having different shapes each of which is sensitive to a different respective stress threshold, thereby allowing a range of stress values to be monitored. FIG. 15 is a diagram of an illustrative configuration for stress sensor 60 with a single bend in link 64. FIG. 16 is a diagram of an illustrative configuration for stress sensor 60 with three bends in link 64. Strips of material with different numbers of bends may have different resistances to stress and may therefore exhibit cracks or other changes upon exceeding different stress thresholds. By incorporating a variety of different sensor types in device 10, stress values in device 10 can be monitored over a range of different stress conditions. As an example, device 10 (e.g. component 66 of FIG. 14, housing 12, display 14, or other structures or devices in device 10) may have a first set of one or more sensors with a straight strain sensing link such as link 64 of FIG. 13, may have a second set of one or more sensors with a single bend link such as link 64 of FIG. 15, may have a third set of one or more sensors with a multiple bend link such as link 64 of FIG. 16, etc. When device 10 is exposed to stress, sensors with lower stress thresholds may be activated (e.g., their links may crack), whereas sensors with higher stress thresholds may not be activated (i.e., their links may remain intact). By evaluating which sensors were activated, the amount of stress experienced in device 10 can be bracketed between lower and higher values.

Figure 17:
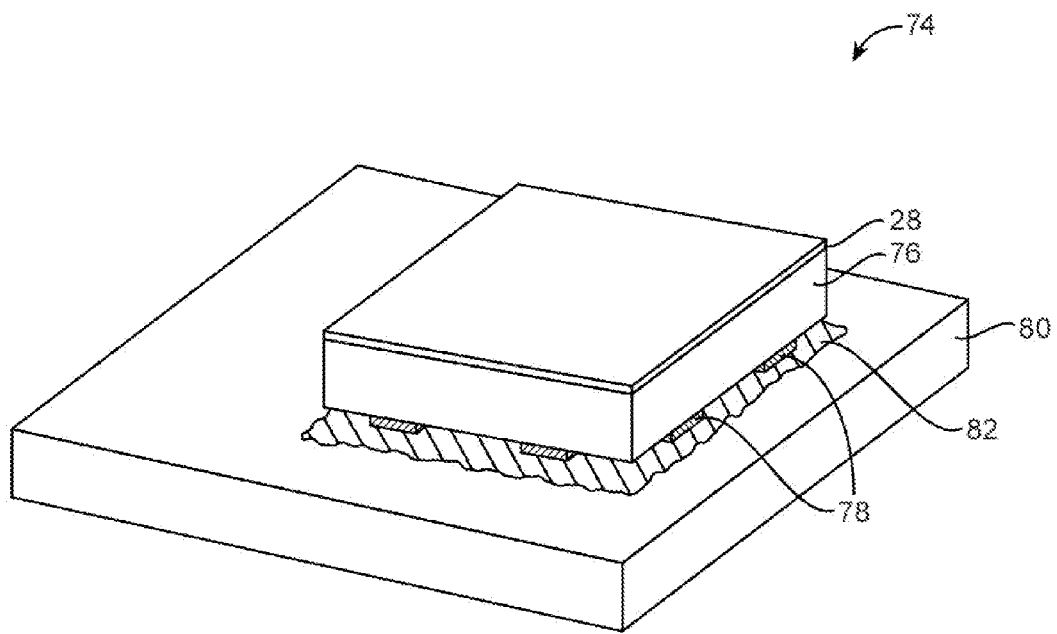
FIG. 17 is a perspective view of an illustrative component with a stress sensing coating in accordance with an embodiment.

FIG. 17 is a perspective view of an illustrative component with a stress sensing structure. In the example of FIG. 17, component 74 includes electrical device 76 mounted to printed circuit 80. Stress sensing coating 28 has been formed on the upper surface of electrical device 76. Device 76 may be a camera, a sensor, a switch, an audio component, a wireless circuit, or other circuitry in device 10. Device 76 may, as an example, be an integrated circuit. Device 76 may be mounted to contacts on printed circuit 80 using solder connections 78. An adhesive such as underfill 82 may be used to help secure device 76 to printed circuit 80. Coating 28 may be an optical thin-film coating that is monitored using reflected light or may be a stress-sensitive coating of the type that develop cracks 56 in response to applied stress. The status of coating 28 may be monitored during testing or may be monitored after device 10 has been used normally by a user (e.g., to determine whether device 10 has been accidentally exposed to excessive stress).

Figure 18:
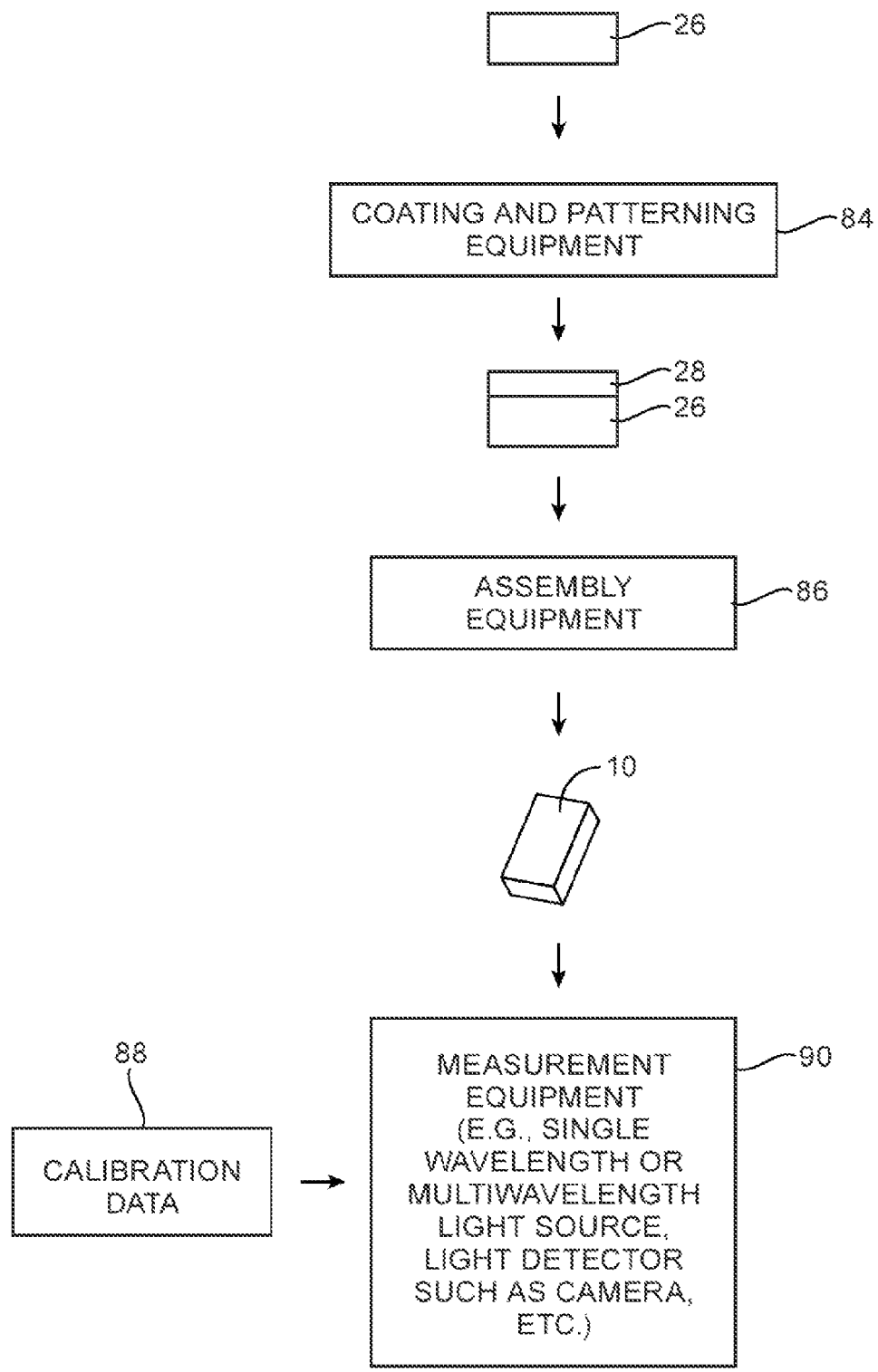
FIG. 18 is a diagram of equipment involved in forming an electronic device and monitoring device structures for stress in accordance with an embodiment.

Illustrative equipment and operations involved in fabricating stress sensing structures for device 10 and in monitoring these structures for exposure to stress are shown in FIG. 18. Initially, structure 26 may be formed. Structure 26 may be a housing structure, a display structure, an internal bracket or other support structure, a component of device 10, an electrical component such as an integrated circuit or other component, or other structure in device 10. Structure 26 may be formed using semiconductor processing techniques, machining, injection molding, etc.

Stress sensing structures may be applied to structure 26 using equipment 84. Equipment 84 may include equipment for depositing thin-film coatings such as transparent thin-film optical coatings of the type that may be optically monitored for interference patterns, may include equipment for depositing inorganic material or other layers of material that crack when subjected to stresses over a predetermined stress threshold, and/or may include equipment for forming patterned stress sensor structures 60 (e.g., equipment for depositing a layer of material and patterning the deposited layer to form sensors with links of various shapes, equipment for attaching pre-patterned stress sensing structures, etc.).

After forming stress sensing coating 28 and/or stress sensor structures 60 on the surface of structure 26, assembly equipment 86 may be used in incorporating these structures into device 10 with the other portions of device 10. Assembly equipment 86 may include computer-controlled positioners, equipment for attaching structures together with adhesive, equipment for attaching structures together using fasteners, soldering equipment, etc.

Calibration data 88 may be obtained by performing bending experiments on known structures under known conditions. These experiments may induce quantifiable levels of stress in the bent structures. Stress sensing structures (e.g., optical coatings, stress-crack coatings, sensor structures 60, etc.) will be affected by the induced stress and the response of these structures can be observed using measurement equipment (e.g., a video imaging device that captures video images, a camera, a microscope or other magnifying equipment, etc.). The stress sensor data from the experiments may be analyzed using data processing equipment and stored in a calibration database. The calibration data in the database may, as an example, quantify which patterns of light interference are associated with certain levels of stress, may quantify which types of stress-induced cracks in coating 28 are associated with certain levels of stress, and/or may quantify which types of stress sensor links 64 are broken (activated) under various levels of stress.

Device 10 can be tested in a partly assembled or fully assembled state. Tests may involve drop tests during which video images are captured to observe optical interference effects in coating 28, drop tests in which cracks in coating 28 are observed during and/or after impact, drop tests in which the state of links 64 in stress sensors 60 is observed during and/or alter impact, bend tests in which the state of stress sensing structures are observed during and/or after bending, and other tests. The stress sensing structures of device 10 may also be affected by stress during use of device 10 by a user (e.g., use by a consumer who is using device 10 under normal operating conditions). During normal operation, device 10 may be accidentally dropped by the user or may otherwise be exposed to forces that give rise to high stress levels in the structures of device 10. Coating 28 (e.g., a coating that develop cracks when over-stressed) and/or stress sensors 60 may be used in monitoring stress during normal use. Stress levels that are monitored in this way can be analyzed when device 10 is examined using measurement equipment (e.g., when device 10 is serviced).

Equipment 90 may include light sources, light detectors (e.g., video imaging equipment), optical inspection equipment and other inspection equipment, computers for performing image analysis operations, stress data analysis operations, and other data processing operations, and other equipment. Equipment 90 may be used to gather stress data from coating 28 and/or sensors 60 in real time during a test and/or may be used to gather stress data from coating 28 and/or sensors 60 following normal usage of device 10 by a user. Equipment 90 may use processing circuitry (e.g., one or more computers or other equipment) to determine what stress levels have been imposed on the structures of device 10. In analyzing the stress data, equipment 90 may use calibration data 88 so that stress levels can be accurately determined. The results of these stress data analysis operations may be used to improve the design of devices such as device 10 or may be used to determine whether or not it is feasible to repair a device that has been damaged due to a drop event or other stress-inducing event.

The foregoing is merely illustrative and various modifications can be made by those skilled in the art without departing from the scope and spirit of the described embodiments. The foregoing embodiments may be implemented individually or in any combination.

What is claimed is:
1. An electronic device, comprising:
a housing;
a display mounted in the housing;
a component mounted in the housing;
a first stress sensing structure including a first layer of material for monitoring stress levels, wherein the first stress sensing structure is configured to monitor stress levels along a first axis; and a second stress sensing structure including a second layer of material for monitoring stress levels, wherein the second stress sensing structure is configured to monitor stress levels along a second axis that is different from the first axis, and wherein at least one of the first and second layers of material comprises a transparent thin-film layer that is a coating on the housing.

2. The electronic device defined in claim 1 wherein at least one of the first and second layers of material of at least one of the first and second stress sensing structures is patterned to form a pair of pads coupled by a strip of the at least one of the first and second layers of material.

3. The electronic device defined in claim 2 wherein the strip includes a bend.

4. The electronic device defined in claim 2 wherein the strip includes multiple bends.

5. The electronic device defined in claim 1 wherein the coating cracks when stressed by more than a predetermined threshold amount.

6. The electronic device defined in claim 5 wherein the coating is an inorganic coating.

7. The electronic device defined in claim 6 wherein the housing has an opening that concentrates stress in the housing and where the inorganic coating is adjacent to the opening.

8. The electronic device defined in claim 1 wherein the first stress sensing structure is formed in a plane that is substantially parallel to the first axis.

9. An electronic device, comprising:
a housing;
a display mounted in the housing;
a component mounted in the housing;
a first stress sensing structure including a first layer of material for monitoring stress levels, wherein the first stress sensing structure is configured to monitor stress levels along a first axis; and
a second stress sensing structure including a second layer of material for monitoring stress levels, wherein the second stress sensing structure is configured to monitor stress levels along a second axis that is different from the first axis, and wherein at least one of the first and second layers of material comprises a transparent thin-film layer that is a coating on the component.

10. The electronic device defined in claim 9 wherein the component comprises an integrated circuit and wherein the coating is formed on the integrated circuit.

11. The electronic device defined in claim 9 wherein the component includes a substrate and wherein the coating is formed on the substrate.

12. An electronic device, comprising:
a housing;
a component mounted in the housing; and
a plurality of stress sensing structures on the component, wherein the stress sensing structures each include a respective link that changes in response to application of stress to the component, wherein the plurality of stress sensing structures comprises a first stress sensing structure having a first link that is not activated in response to application of stress below a first threshold and that is activated in response to application of stress that exceeds the first threshold, and a second stress sensing structure having a second link that is not activated in response to application of stress below a second threshold and that is activated in response to application of stress that exceeds the second threshold that is different from the first threshold.

13. The electronic device defined in claim 12 wherein the component comprises a substrate on which the stress sensing structures are mounted and includes an integrated circuit on the substrate.

14. The electronic device defined in claim 12 wherein each of the stress sensing structures is formed from a patterned layer of material, wherein each of the stress sensing structures has a pair of pads, and wherein the link of each stress sensing structure extends between the pads.

15. The electronic device defined in claim 14 wherein the link of each of the stress sensing structures has a different respective shape.

16. The electronic device defined in claim 15 wherein at least some of the links comprises strip-shaped links of different respective lengths.

17. A method of testing an electronic device, comprising:
coating at least one structure in the electronic device with a transparent thin-film coating;
illuminating the coating with monochromatic light; and
applying stress to the structure in an impact event in which the electronic device impacts a stationary object while gathering images of the coating with a light detector.

18. The method defined in claim 17 wherein the structure comprises an electronic device housing in the electronic device and wherein the monochromatic light is reflected from the electronic device housing, the method further comprising analyzing the gathered images to measure optical interference patterns in the reflected monochromatic light.

* * * * *